United States Patent [19]

Crawford et al.

[11] Patent Number: 4,489,875
[45] Date of Patent: Dec. 25, 1984

[54] SELF-CENTERING SURGICAL STAPLE AND STAPLER FOR APPLYING THE SAME

[75] Inventors: John O. Crawford, Bookfield Center; Roy D. Gravener, Bethany, both of Conn.

[73] Assignee: United States Surgical Corporation, Norwalk, Conn.

[21] Appl. No.: 381,865

[22] Filed: May 25, 1982

Related U.S. Application Data

[63] Continuation of Ser. No. 194,407, Oct. 17, 1980, abandoned.

[51] Int. Cl.³ .............................................. A61B 17/10
[52] U.S. Cl. ........................... 227/19; 128/334 R; 128/337; 411/472; 227/83; 227/DIG. 1
[58] Field of Search ............... 128/334 R, 337, 335; 411/472, 470, 471, 473–476, 457; 227/DIG. 1, 83, 19

[56] References Cited

U.S. PATENT DOCUMENTS

| | | | |
|---|---|---|---|
| 517,836 | 4/1894 | Bradish | 411/472 X |
| 733,723 | 7/1903 | Lukens | 128/337 |
| 1,910,688 | 5/1933 | Goodstein | 411/474 |
| 2,380,655 | 7/1945 | Lang | 411/472 |
| 3,154,999 | 11/1964 | Stewart | 411/474 |
| 3,363,628 | 1/1968 | Wood | 128/325 |
| 3,643,851 | 2/1972 | Green et al. | 227/19 |
| 3,650,453 | 3/1972 | Smith | 227/138 |
| 3,837,555 | 9/1974 | Green | 227/130 |
| 4,014,492 | 3/1977 | Rothfuss | 227/DIG. 1 |
| 4,263,903 | 4/1981 | Griggs | 128/334 R X |
| 4,317,451 | 3/1982 | Cerwin et al. | 128/325 |
| 4,407,286 | 10/1983 | Noiles et al. | 227/83 X |

FOREIGN PATENT DOCUMENTS

| | | | |
|---|---|---|---|
| 737897 | 10/1955 | United Kingdom | 89/2 |
| 178032 | 2/1966 | U.S.S.R. | 128/337 |

Primary Examiner—Michael H. Thaler
Attorney, Agent, or Firm—John E. Nathan; Stephen P. Gilbert

[57] ABSTRACT

An improved, self-centering surgical staple is disclosed. Engaging members are located on the base portion of the staple. During forming (bending) of the staple on the anvil, the engaging members engage the forming mechanisms (i.e., the shoulders of the anvil or the twin heads of the pusher) to center the staple on the anvil so that the legs will be embedded in the tissue at the same depth.

8 Claims, 19 Drawing Figures

SELF-CENTERING SURGICAL STAPLE AND STAPLER FOR APPLYING THE SAME

This is a continuation of application Ser. No. 194,407, filed Oct. 17, 1980, now abandoned.

BACKGROUND OF THE INVENTION

This invention relates to surgical staples of the type which are bent around an anvil by a pusher in a surgical stapler.

Surgical staplers for applying staples to close incisions or wounds in body tissue are shown, for example, in Green et al. U.S. Pat. No. 3,643,851, Smith, U.S. Pat. No. 3,650,453, Green U.S. Pat. No. 3,837,555 and Noiles et al. U.S. patent application Ser. No. 181,092, filed Aug. 25, 1980, now abandoned, entitled "Improved Surgical Staples." Such staples have become widely known and used in recent years and typically are preformed and have a broad-based square-cornered "U" shape.

In the staplers, the staple is urged toward an anvil by a bifurcated pusher with a generally "U"-shaped recess between its twin heads. The base of the "U"-shaped recess in the pusher is broader than the anvil but not as broad as the base of the "U"-shaped staple. When the staple reaches the anvil, the heads of the bifurcated pusher cause the staple to bend around the anvil into a closed, square-cornered "C" or rectangular shape.

During bending, the ends of the staple enter the tissue, below the anvil, and draw the tissue on opposite sides of the wound or incision together. After bending is complete, the pusher is retracted from the staple and the anvil is slid out from within the staple. The staple remains in the tissue to hold it together during healing.

However, a significant problem is that the staples frequently are not bent symmetrically about the anvil because the staple becomes off-center during forming. As a result, the sharp ends of the staples are misaligned within the tissue being stapled, one end being too deeply embedded in the tissue and the other end not deeply enough.

SUMMARY OF THE INVENTION

An improved, self-centering surgical staple has now been developed. The staple comprises a base and a pair of legs connected to the base. Engaging means are located on the base to engage the forming means, i.e., the shoulders of the anvil (the corners of the top or proximal side of the anvil) or the twin heads of the pusher. The engaging means are symmetrically located about the transverse centerline of the staple.

When application of the staple to a patient is commenced, the pusher touching the staple against the anvil often causes the staple to move longitudinally (i.e., along its length) on the anvil and, thus, become off-centered and, ultimately, misaligned within the tissue. In the new staple, however, should such movement occur, one of the engaging means immediately catches (or engages) one of the heads of the pusher or one of the shoulders of the anvil, depending on where the engaging means are located. That retains the staple in place during the rest of the forming procedure and ensures that the clip is symmetrically bent around the anvil, since the engaging means are symmetrically located on the base of the staple. In preferred embodiments, the engaging means are grooves in the upper or lower side of the base or raised projections on the lower side of the staple.

BRIEF DESCRIPTION OF THE DRAWINGS

In FIG. 1, the staple is viewed from above with one of the ends of the staple closer than the base of the staple.

In FIG. 5, the staple has been bent into a closed "C" shape and embedded in tissue by the stapler.

In FIG. 13, the staple has been bent into a closed "C" shape and embedded in tissue by the stapler.

In FIG. 14, the staple is viewed from beneath, with the left portion of the base of the staple closer than the ends of the staple.

In FIG. 19, the staple has been bent into a closed "C" shape and embedded in tissue by the stapler.

DETAILED DESCRIPTION OF THE INVENTION

Figure 1:
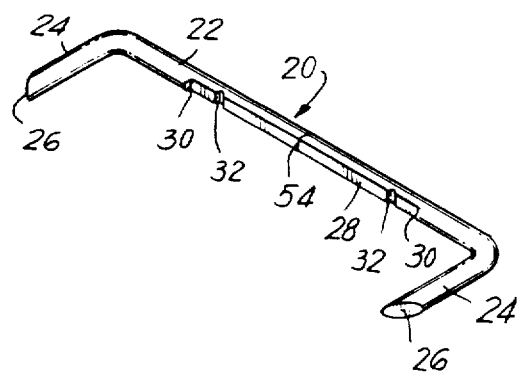
FIG. 1 is a perspective view of one embodiment of the improved surgical staple of this invention.

One embodiment, generally 20, of the surgical staple of this invention is shown in FIG. 1. Staple 20 is made of metal wire and has a generally round cross-section. Base 22 and parallel legs 24 are at right angles. The ends of legs 24 are cut off at an angle to provide sharp tips 26, which allow staple 20 to penetrate tissue more easily and cleanly. A typical material for the staple is 316L stainless steel wire having a diameter of 0.020 or 0.022 inches. Other materials and dimensions will be apparent to those skilled in the art.

In accordance with this invention, staple 20 is provided with grooves 32 on base 22 for engaging the shoulders of the anvil of a stapler, as will be described below. Grooves 32 are spaced apart symmetrically about imaginary transverse centerline 54. Each is approximately the same distance from its adjacent leg 24. Grooves 32 are preferably transverse to base 22. (As used herein, "transverse" means perpendicular to the length of the base portion of the staple and "longitudinal" means in the direction of the length.)

Base 22 of staple 20 also includes two spaced surfaces 30, which are preferably transverse to base 22. Transverse surfaces 30 are symmetrical about imaginary centerline 54, and each is located between one of the grooves 32 and the leg 24 closest to that groove. Use of such surfaces in the staple allows the pusher to be retracted from the staple after application is complete and is preferred but forms no part of the present invention. The preferred location, orientation, and spacing of transverse surfaces 30 are described in Noiles et al. U.S. patent application, Ser. No. 181,092, filed Aug. 25, 1980, entitled "Improved Surgical Staples."

Grooves 32 are located within a recessed portion of base 22 defined by flat surface 28 delimited by transverse surfaces 30. Although surface 28 is preferably smooth and flat (except for the grooves 32) this is not required. Surface 28 may have any characteristic which will not interfere with stapling.

Figure 2:
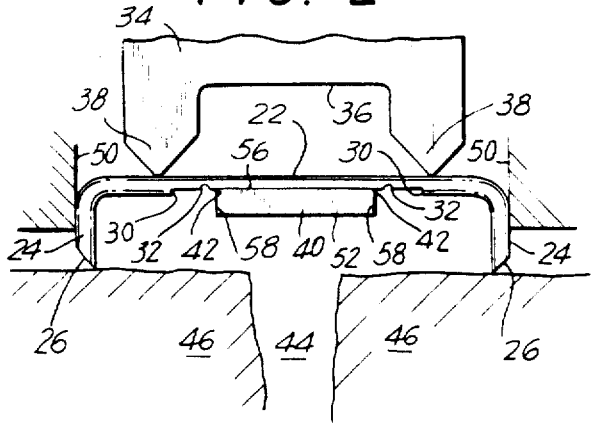
FIGS. 2 to 5 are schematic views of the use of the staple of FIG. 1.

The use of staple 20 with a stapler is schematically shown in FIGS. 2 to 5. In FIG. 2, staple 20 is urged towards anvil 40 between parallel guides 50 by movement of the bifurcated pusher 34 towards the anvil. Pusher 34 and anvil 40 comprise the staple forming means. Pusher 34 has twin heads 38 and recess 36 therebetween. The distal side 52 of the anvil 40 is adjacent to the skin tissue 46 to be stapled. The anvil is positioned so that one of the staple legs 24 is on each side of incision or wound 44 to be closed, with sharp tips 26 of staple legs 24 pointing towards the tissue. Legs 24 of the staple are located symmetrically about anvil 40.

With this orientation and alignment of staple 20, surface 28 of the recessed portion of the staple faces the proximal side 56 of the anvil, and the grooves 32 are equally spaced from the lateral sides 58 and shoulders 42 of the anvil. Of necessity, transverse surfaces 30 are equally spaced from lateral sides 58. (It should be understood that in FIG. 2 the spacing of grooves 32 beyond shoulders 42 is for clarity only and that an actual staple will have the grooves much closer to the shoulders.)

Figure 3:
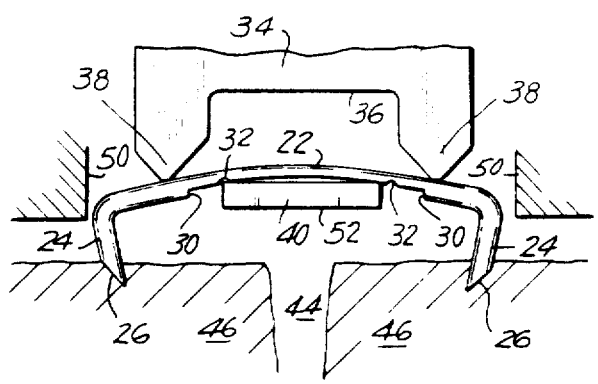

When the pusher first contacts the staple with the anvil, base 22 tends to move longitudinally, towards one of the heads 38 of pusher 34. However, as shown in FIG. 3, such movement is halted when left groove 32 engages the adjacent shoulder 42 of anvil 40.

Figure 4:
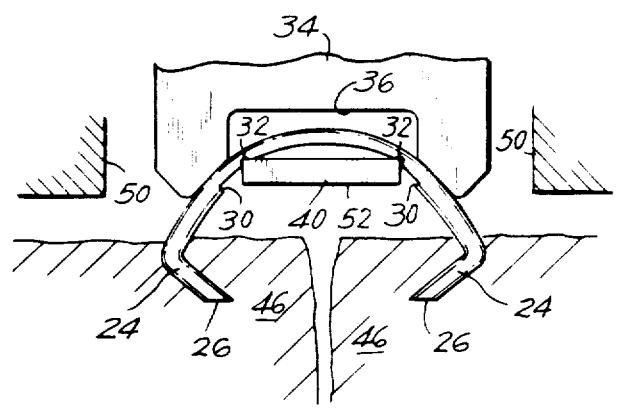

As seen in FIG. 4, the force of pusher 34 continuing to move toward anvil 40 while one groove 32 engages shoulder 42 causes arching of base 22. The arching increases until right groove 32 engages the other shoulder of anvil 40. At this point in bending staple 20, base 22 is symmetrically disposed (centered) about anvil 40, as shown in FIG. 4. This self-centering of the staple 20 is most desirable because it ensures that the legs will be embedded at the same depth in the tissue.

Figure 5:
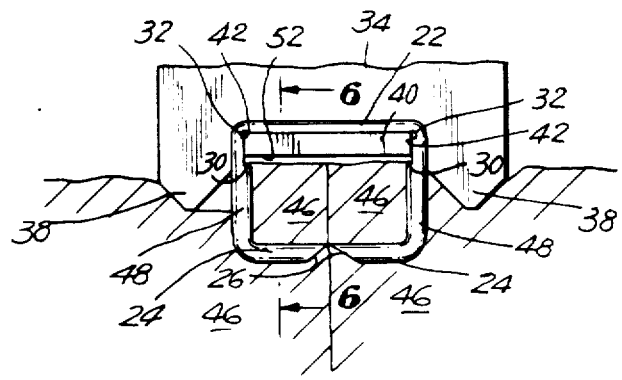

In FIG. 5, further movement of pusher 34 towards the anvil 40 has caused heads 38 to wrap outer extending portions 48 of base 22 around the lateral sides of the anvil. Staple 20 has been bent into a closed "C" shape and embedded in the tissue 46, legs 24 have been embedded in tissue 46 at substantially the same depth, and wound or incision 44 has been closed. Transverse surfaces 30 of the staple are below the distal side 52 of the anvil. When staple pusher 34 is retracted to release the stapler from the staple, transverse surfaces 30 engage the corners of the distal side of the anvil to prevent the staple from being pulled out of the patient due to the frictional engagement of staple sides 48 by the pusher.

Figure 6:
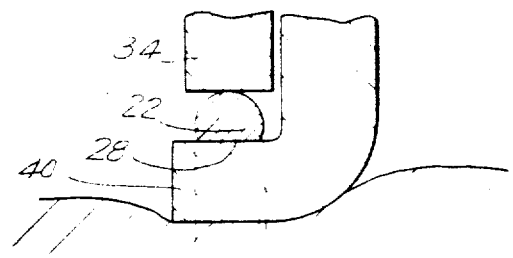
FIG. 6 is a sectional view taken along line 6—6 in FIG. 5.
Figure 7:
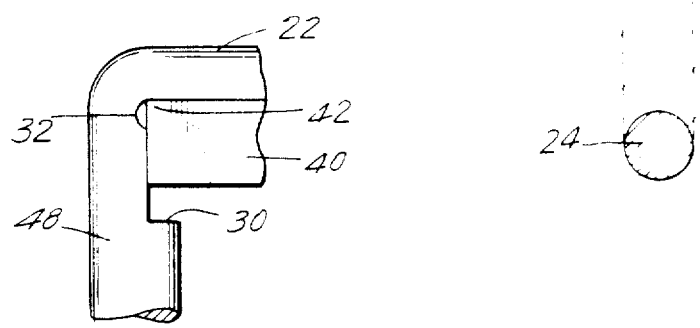
FIG. 7 is fragmentary view showing the relationship between the base of the staple and the anvil of the stapling apparatus after the staple has been bent into a closed "C" shape.

FIG. 6 shows surface 28 of base 22 forced against anvil 40 by pusher 34. FIG. 7 shows groove 32 located adjacent anvil shoulder 42 and transverse surface 30 below the distal side of anvil 40 after forming of the staple around the anvil has been completed.

The configuration of the staple shown in FIGS. 1–7 has other advantages besides being self-centering. The substantially flat surface 28, which contacts anvil 40, stabilizes the staple on the anvil during forming. This reduces the possibility that the staple may roll or twist on the anvil as it is being bent and forced into the tissue. It also reduces the possibility that a staple may slip off the anvil before it has been fully bent and the stapler removed from the staple.

Figure 8:
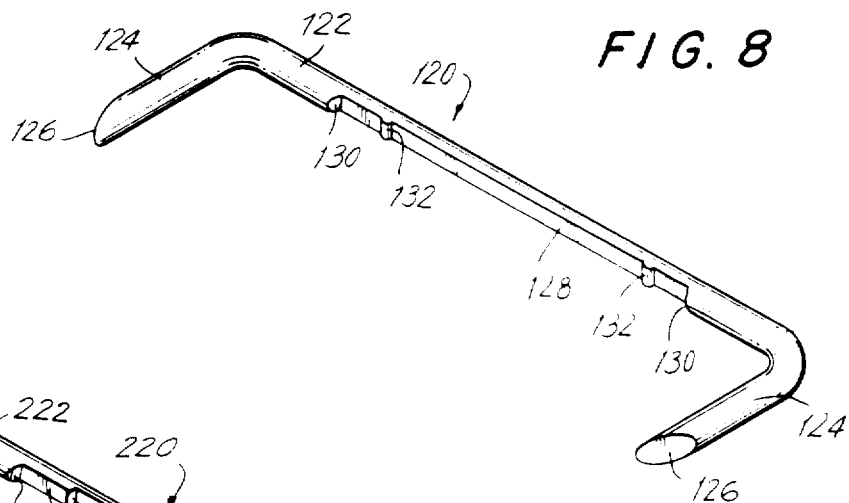
FIGS. 8 to 10 are perspective views of other embodiments of the staple of this invention.

FIG. 8 shows another embodiment, generally 120, of a staple of this invention. Like staple 20 of FIG. 1, staple 120 of FIG. 8 comprises base 122 and parallel legs 124 having sharp tips 126. Staple 120 also has transverse surfaces 130 and flat recessed surface 128 between them. The only difference between staple 120 of FIG. 8 and staple 20 of FIG. 1 is that the means 132 for engaging the shoulders of the anvil comprises a pair of elevated projections or ridges on the recessed surface 128 as compared to grooves in recessed surface 28. However, the ridges 132 perform the same function in virtually the same way as the grooves 32 of staple 20. Preferably, the ridges 132 are elevated about 0.002 to about 0.003 inches above the recessed surface 128 of base 122 and are about 0.10 inches wide. Smaller or larger ridges could also be utilized.

Figure 9:
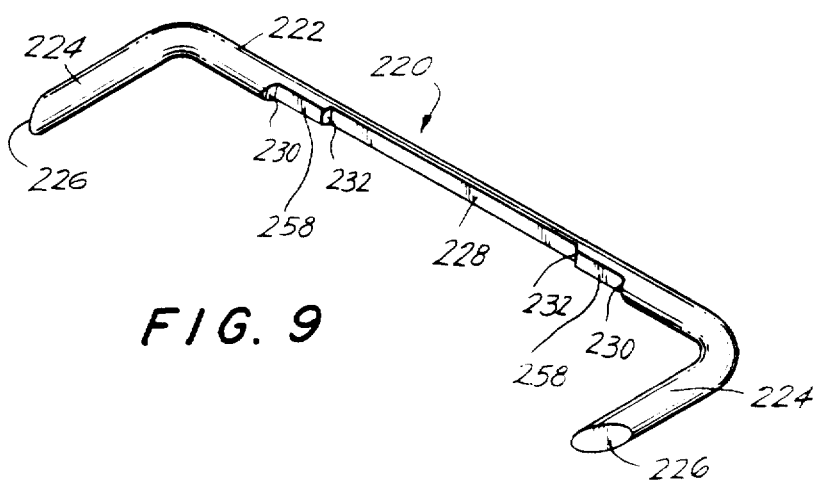

Shown in FIG. 9 is another embodiment, generally 220, of the staple of this invention. Staple 220 comprises base 222 and a pair of parallel legs 224 having sharp tips 226. Staple 220 also has transverse surfaces 230 and flat recessed surfaces 258 between transverse surfaces 230. The only difference between staple 20 of FIG. 1 and staple 220 of FIG. 9 is that the means on the base 222 for engaging the forming means (in this case, the shoulders of the anvil) comprises a second pair of transverse surfaces 232 at the ends of a second flat more recessed surface 228.

Figure 10:
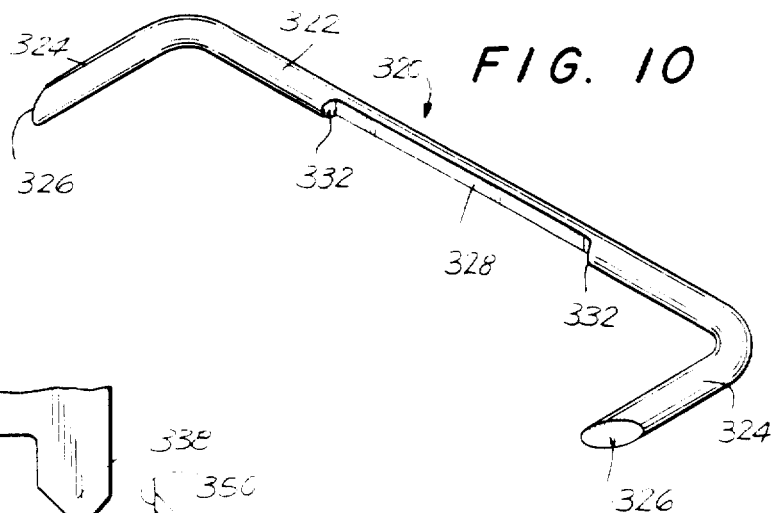

Shown in FIG. 10 is an another embodiment, generally 230, of a staple of this invention. Staple 320 is similar to staple 20 of FIG. 1 and can be used in a similar manner for stapling tissue. Staple 320 comprises base 322 and a pair of parallel legs 324 having sharp tips 326. Staple 320 also includes recessed surface 328 and means on base 322 for engaging the forming means (in this case, the shoulders of the anvil). The engaging means comprises a pair of transverse surfaces 332 as in staple 220 of FIG. 9, not grooves as in staple 20 of FIGS. 1–7.

Figure 11:
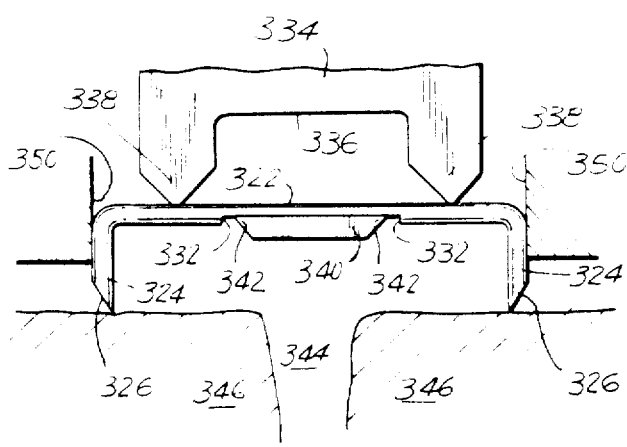
FIGS. 11 to 13 are schematic views of the use of the staple of FIG. 10.
Figure 12:
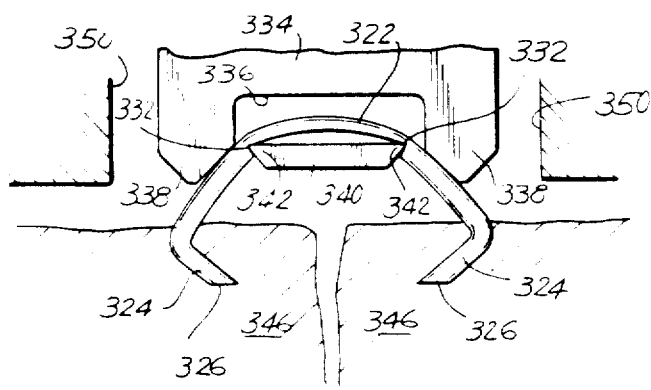
Figure 13:
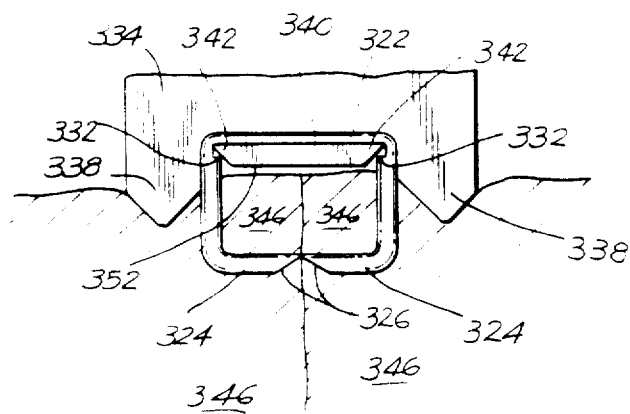

FIGS. 11 to 13 show embedding staple 320 in tissue 346 using a stapler with trapezoidal anvil 340, conventional guides 350, and conventional bifurcated pusher 334 with twin heads 338 and recess 336 therebetween.

In FIG. 11 pusher 334 has forced staple base 322 against anvil 340 and sharp tips 326 rest on tissue 346 surrounding wound or incision 344. Flat surface 328 (FIG. 10) rests on the proximal (upper) side of the anvil, with transverse surfaces 332 lying just beyond anvil shoulders 342.

In FIG. 12 pusher heads 338 have moved towards anvil 340 to such an extent that base 322 has bowed and legs 324 have been forced into tissue 346, closing the wound. By this point, surfaces 332 have engaged shoulders 342 to ensure that the clip is centered. (Longitudinal movement of the clip generally occurs when the heads first contact the clip with the anvil.)

In FIG. 13, the staple is completely embedded in tissue 346 with the staple tips aligned. Distal side 352 of the anvil is near the surface of tissue 346. Surfaces 332, located inwardly of anvil shoulders 342, prevent the staple from being pulled out of the tissue 346 when pusher 334 is retracted. This function of surfaces 332 is in addition to centering the staple on the anvil (FIG. 12).

FIGS. 14–19 show another embodiment, generally 420, of a staple of this invention. Staple 420 comprises base 422 and a pair of parallel legs 424 having sharp tips 426. Staple 420 also has transverse surfaces 430 at the ends of recessed surface 428 as well as means for engaging the forming means (in this case, the twin heads 438 of pusher 434) when the pusher urges staple base 422 against anvil 440. The engaging means comprises grooves 432 on the side of the base 422 remote from legs 424, i.e., on the proximal (upper) side of the staple in FIG. 15.

Figure 15:
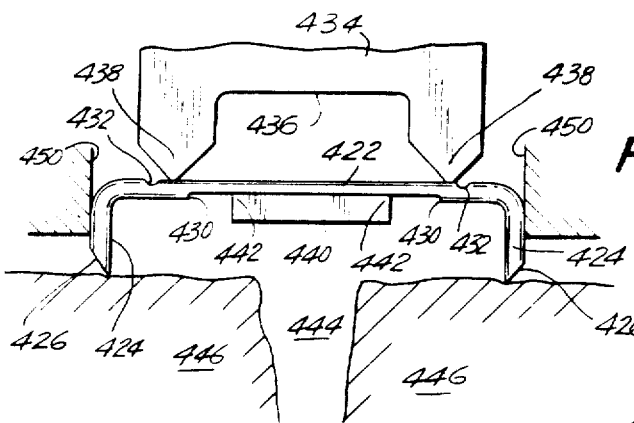
FIGS. 15 to 19 are schematic views of the use of the staple of FIG. 14.
Figure 14:
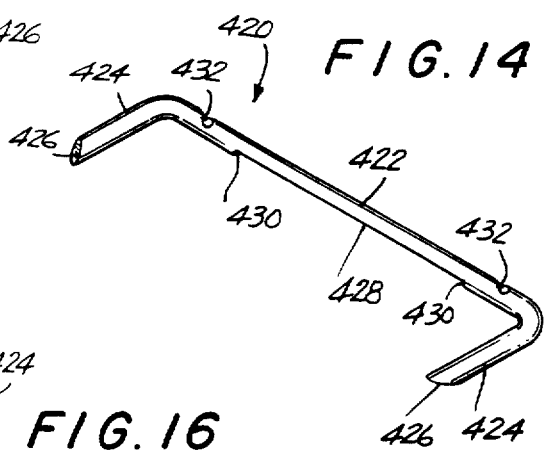
FIG. 14 is a perspective view of another embodiment of the staple of this invention.

In FIG. 15 the staple 420 is held between guides 450 of a conventional stapler in which a bifurcated pusher 434 having twin heads 438 separated by recess 436 urges base 422 of staple 420 against anvil 440 of the stapler. Tips 426 rest on tissue 446 surrounding wound or incision 444.

Figure 16:
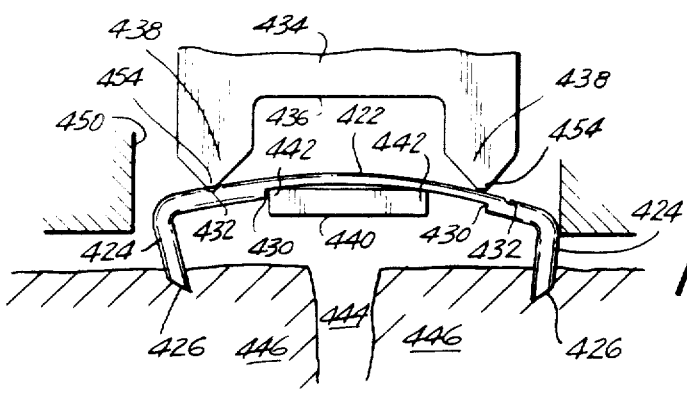

When the heads of the pusher first contact the staple, base portion 422 tends to move longitudinally to the right on the anvil until it is restrained by the left groove 432 engaging the narrow tip 454 of left head 438 of the pusher (see FIG. 16).

Figure 17:
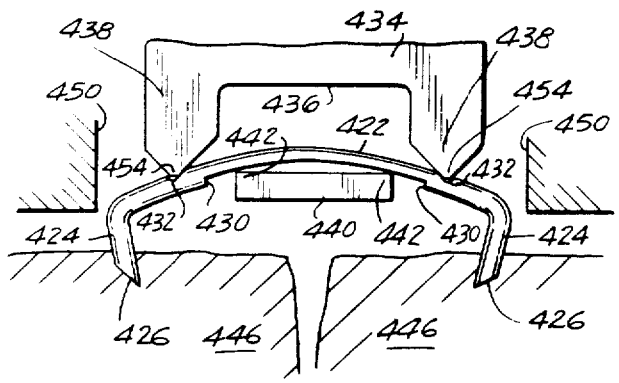
Figure 18:
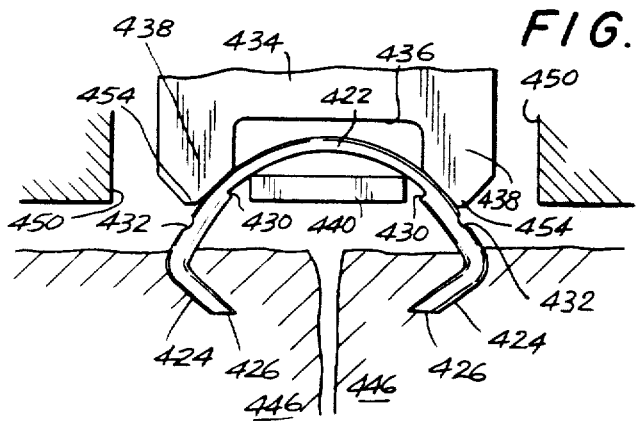
Figure 19:
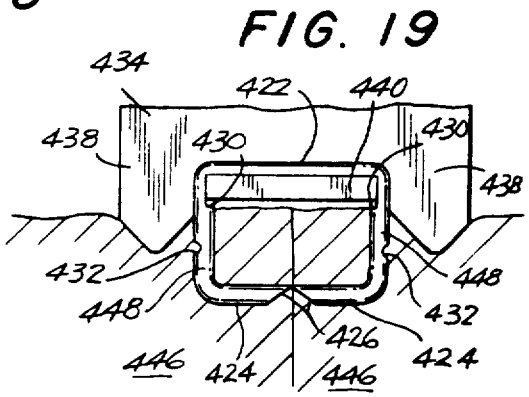

Thereafter, as shown in FIG. 17, as base 422 becomes more curved, right groove 432 moves to the left until it engages tip 454 of right head 438. At this point, the staple is centered. Deformation of the base continues (FIG. 18) until staple 420 is completely embedded in tissue 446 with its legs 424 aligned (FIG. 19).

In accordance with this invention, particular dimensions for the engaging means (e.g., grooves 32 in FIG. 1) and particular spacings between them and locations in the staple are not critical but should be within certain limits. The engaging means can have any size and shape that will ensure that one of the two engaging means will (a) engage one of the two shoulders of an anvil or one head of a bifurcated pusher when the staple base moves longitudinally during forming and (b) restrain such longitudinal movement while the base arches to bring the second engaging means into contact with the second shoulder of the anvil or the second head of the pusher, thereby recentering the staple.

The engaging means should be positioned to prevent excessive longitudinal movement before engagement with the forming means halts such movement. The engaging means will preferably be symmetrically located in the base of the staple with respect to the transverse centerline of the base. Where the means are to engage the shoulders of the anvil, the means should be spaced so that when the staple is centered on the anvil before forming, the means on each side extends beyond the shoulder by a distance equal to one-half [L(arc) minus L(chord)], where L(arc) is the arc-length on the base of the staple between the two means at maximum bowing of the base and L(chord) is the chord length between the means at the same time.

It will be understood that the embodiments shown and described herein are merely illustrative of the principles of the invention and that various modifications can be made by those skilled in the art without departing from the spirit and scope of the invention. For example, the invention is not limited to staples having an initially square-cornered "U" shape. Staples preformed with other shapes may be utilized. The various means 32, 132, 232, 332, and 432 for engaging the forming means might have means for ensuring the engagement, e.g., roughened surfaces.

We claim:

1. In combination:
   (a) a surgical stapler having means for forming a surgical staple as the staple is applied to a patient, said means comprising a pusher and an anvil having shoulders about which the staple is bent by the pusher during application of the staple; and
   (b) a self-centering surgical staple comprising a base and a pair of legs connected to the base, said base having two means spaced from the legs and symmetrically located about the transverse centerline of the base for engaging the forming means to center the staple on the anvil as the staple is applied to the patient wherein the engaging means are on the side of the base contacted by the shoulders of the anvil during application of the staple.

2. The combination of claim 1 wherein the engaging means are grooves.

3. The combination of claim 1 wherein the engaging means are raised projections.

4. In combination,
   (a) a surgical stapler having means for forming a surgical staple as the staple is applied to a patient, said means comprising a pusher and an anvil having shoulders about which the staple is bent by the pusher during application of the staple; and
   (b) a self-centering surgical staple comprising a base and a pair of legs connected to the base, said base having two means spaced from the legs and symmetrically located about the transverse centerline of the base for engaging the forming means to center the staple on the anvil as the staple is applied to the patient wherein the two engaging means are positioned on the base so that when the staple is centered on the anvil before forming, each engaging means extends beyond its respective anvil shoulder by a distance equal to one-half of ($L_{arc}$ minus $L_{chord}$), where $L_{arc}$ is the arc-length on the base of the staple between the engaging means at maximum bowing of the base during forming and $L_{chord}$ is the chord-length between the engaging means at the same time.

5. In combination,
   (a) a surgical stapler having means for forming a surgical staple as the staple is applied to a patient, said means comprising a pusher and an anvil having shoulders about which the staple is bent by the pusher during application of the staple; and
   (b) a self-centering surgical staple comprising an essentially linear base and a pair of legs connected to the ends of the base, said base having two means spaced from the legs and symmetrically located about the transverse centerline of the base for engaging the forming means to center the staple on the anvil as the staple is applied to the patient wherein the engaging means are on the side of the base contacted by the shoulders of the anvil during application of the staple.

6. The combination of claim 5 wherein the engaging means are grooves.

7. The combination of claim 5 wherein the engaging means are raised projections.

8. In combination,
   (a) a surgical stapler having means for forming a surgical staple as the staple is applied to a patient, said means comprising a pusher and an anvil having shoulders about which the staple is bent by the pusher during application of the staple; and
   (b) a self-centering surgical staple comprising an essentially linear base and a pair of legs connected to the ends of the base, said base having two means spaced from the legs and symmetrically located about the transverse centerline of the base for engaging the forming means to center the staple on the anvil as the staple is applied to the patient wherein the two engaging means are positioned on the base so that when the staple is centered on the anvil before forming, each engaging means extends beyond its respective anvil shoulder by a distance equal to one-half of ($L_{arc}$ minus $L_{chord}$), where $L_{arc}$ is the arc-length on the base of the staple between the engaging means at maximum bowing of the base during forming and $L_{chord}$ is the chord-length between the engaging means at the same time.

* * * * *